(12) United States Patent
Haff

(10) Patent No.: US 8,284,895 B1
(45) Date of Patent: Oct. 9, 2012

(54) ONE DIMENSIONAL LINESCAN X-RAY DETECTOR

(75) Inventor: Ronald P. Haff, Davis, CA (US)

(73) Assignee: The United States of America, as represented by the Secretary of Agriculture, Washington, DC (US)

(*) Notice: Subject to any disclaimer, the term of this patent is extended or adjusted under 35 U.S.C. 154(b) by 217 days.

(21) Appl. No.: 12/543,332

(22) Filed: Aug. 18, 2009

Related U.S. Application Data

(60) Provisional application No. 61/089,793, filed on Aug. 18, 2008.

(51) Int. Cl.
*G01B 15/06* (2006.01)
*G01N 23/083* (2006.01)

(52) U.S. Cl. ............... 378/54; 378/58; 382/110

(58) Field of Classification Search ........... 378/51, 378/53, 54, 56, 62, 207, 210; 382/110, 128, 382/132, 141–143, 145, 149; 426/231, 240; 250/253–266, 306–308, 442.11, 362, 371
See application file for complete search history.

(56) References Cited

U.S. PATENT DOCUMENTS

| | | | | |
|---|---|---|---|---|
| 3,768,645 | A * | 10/1973 | Conway et al. | 209/565 |
| 4,666,045 | A * | 5/1987 | Gillespie et al. | 209/585 |
| 6,445,765 | B1 * | 9/2002 | Frank et al. | 378/56 |
| 6,449,334 | B1 * | 9/2002 | Mazess et al. | 378/53 |
| 6,973,161 | B2 * | 12/2005 | Ohtsuki | 378/57 |
| 7,024,942 | B1 * | 4/2006 | Jackson et al. | 73/818 |
| 2002/0008055 | A1 * | 1/2002 | Campbell et al. | 209/577 |
| 2009/0257621 | A1 * | 10/2009 | Silver | 382/103 |
| 2009/0315229 | A1 * | 12/2009 | Tomasic | 266/44 |

OTHER PUBLICATIONS

Serway, Raymond A., et al., College Physics Fifth Edition, 1999, Harcourt Brace College Publishers, Saunders College Publishing, pp. 709-711.*

* cited by examiner

*Primary Examiner* — Anastasia Midkiff
(74) *Attorney, Agent, or Firm* — Elizabeth R. Sampson; Leslie Shaw; John D. Fado

(57) ABSTRACT

The present invention relates to an x-ray detector configured to generate one-dimensional x-ray density profiles. In exemplary embodiments the x-ray detector is used for the purpose of detecting inclusions in agricultural commodities.

8 Claims, 2 Drawing Sheets

ONE DIMENSIONAL LINESCAN X-RAY DETECTOR

FIELD OF THE INVENTION

The invention relates to an x-ray detector array configured to produce real-time one dimensional x-ray density profiles of samples for detection of inclusions. In an exemplary embodiment, the x-ray detector configuration is used for sorting purposes.

BACKGROUND OF THE INVENTION

In recent years, x-ray inspection has become increasingly common in certain segments of the food industry. In particular, because of the ever-increasing emphasis on food safety, processed foods, including e.g., products that are packaged in cans, bottles, or jars, are typically x-ray inspected.

X-ray inspection is superior to traditional metal detection technology for the detection of metallic contaminants, and is also effective for detection of non-metallic material such as e.g., bone, glass, wood, plastic, and rocks. Indeed, technological advances in the areas of high voltage power supplies, solid-state detectors, and computation power and speed have made x-ray systems more affordable, reliable, and easier to use while improving image quality and detection capabilities. A variety of improvements in sensor technology have improved resolution, including CsI crystals and improved CCD arrays.

In a typical linescan x-ray machine, a two dimensional image of an object or objects are created using hundreds or thousands of detectors, e.g., photodiodes overlaid with phosphor or semiconductor crystals, placed in a row perpendicular to the direction of sample flow. As the sample moves between the x-ray source and the detector array at a fixed rate, the output of the photodiodes are repeatedly scanned at a rate synchronized to the speed of the sample. The two dimensional image is then constructed row by row. Creation of the image is thus dependant on the motion of the sample across the line of detectors. Most high-speed applications employ a side view arrangement, as opposed to a top view system since this way the conveyor belt is not included in the image.

Forming a two-dimensional image requires timing the scanning of the detector array to the motion of the sample and tracking the output of each individual photodiode for each scan. Thus, two dimensional x-ray imaging is complicated, and adds a great deal of cost and complexity to the sorting/inspecting apparatus. Indeed, linescan x-ray machines for food inspection are bulky and expensive and their incorporation into an existing food processing line is often disruptive. What's more, it is often the case that a two dimensional image is not required to accomplish the inspection/sorting task. Thus the degree of complication and sophistication embodied by linescan x-ray machines is frequently unnecessary.

Therefore, what is needed in the art is an effective, less expensive and less complicated x-ray based sorting/inspection device. Fortunately, as will be clear from the following disclosure, the present invention provides for this and other needs.

SUMMARY OF THE INVENTION

Thus, in an exemplary embodiment, the invention provides an apparatus for detecting pits in cherries. The apparatus comprises (i) an x-ray source, (ii) a linescan detector array configured so that the sum of the outputs of the photodiodes is read for each scan, (iii) a microprocessor which applies a decision algorithm based on the characteristics of the input signal, (iv) a diversion mechanism, and (v) required radiation shielding.

In another embodiment, the invention provides an apparatus for detecting defects or contaminants in agricultural products based on the characteristics of a one-dimensional signal generated by the detector array as the sample passes between the x-ray source and the array. The apparatus comprises (i) an x-ray source, (ii) a linescan detector array configured so that the sum of the outputs of the photodiodes is read for each scan, (iii) a microprocessor which applies a decision algorithm based on the characteristics of the input signal, (iv) a diversion mechanism, and (v) required radiation shielding.

The use of x-ray imaging systems for the inspection of agricultural products to detect defects or contaminants is an area of active research. Much of this work involves the creation and application of computer algorithms that analyze the two-dimensional image and generate a decision signal based on that analysis. These types of applications are well known in the art (see e.g., Haff, R. P. and D. C. Slaughter, (2004), *Trans. ASAE* 47(2):531-537 or Haff, R. P. and T. C. Pearson, (2007), *Sens. & Instrumen. Food Qual.* 1:143-150).

Disclosed herein is an alternative to the two dimensional x-ray imaging systems known in the art. Indeed, the instant disclosure provides imaging systems that utilize the generation of a one-dimensional signal rather than a two-dimensional image, thus simplifying both the imaging process and also the creation of decision algorithms based on the signal. Thus, this approach is superior for imaging objects that are readily analyzed in one-dimension e.g., objects that are distinguished by virtue of having a void in the center, or not, e.g., cherries having pits in the center wherein the cherries with pits are distinguished from cherries without pits, the cherries without pits having a void in the center.

Other features, objects and advantages of the invention will be apparent from the detailed description which follows.

DETAILED DESCRIPTION OF THE INVENTION

Definitions

Figure 1:
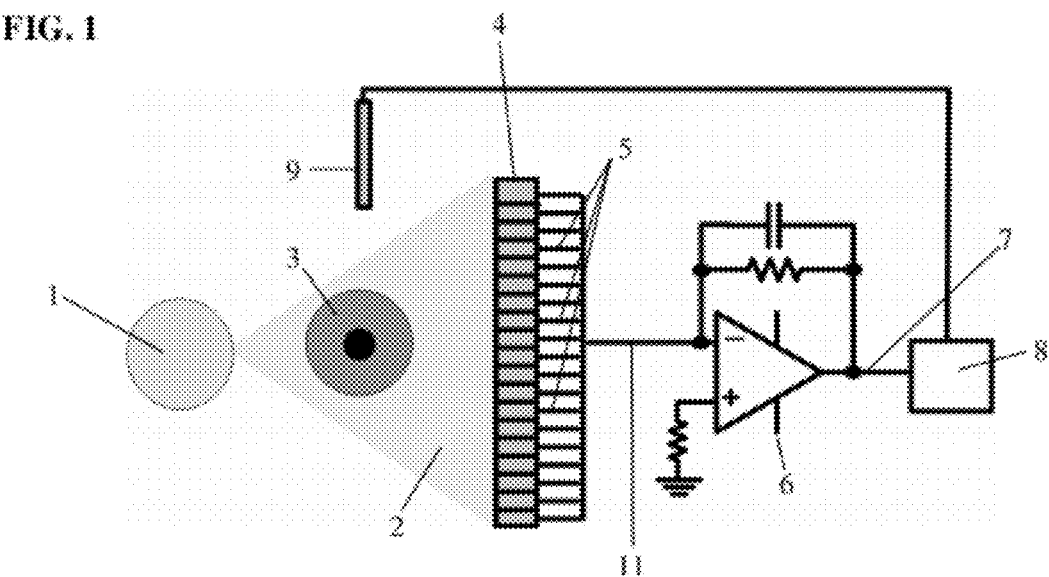
FIG. 1. Schematic view illustrating a linescan x-ray based sorting device with detectors configured to generate a one-dimensional x-ray density profile of the sample, as opposed to a traditional two-dimensional image.

Unless otherwise noted, technical terms are used according to conventional usage. Definitions of common terms in electronics and telecommunications sciences may be found in e.g., Federal Standard 1037C, *Glossary of Telecommunication Terms*, 1996, which is incorporated herein by reference.

The term "x-ray source" as used herein refers to an x-ray tube energized by a high voltage power supply.

The expression "population to be sorted" as used herein refers to a population of objects e.g. a population of agricultural products, e.g., cherries, peaches, apricots, etc; a population of canned goods, a population of bottled goods, etc, the composition of which is heterogeneous. A "heterogeneous" population typically comprises more than one type or category of object. In an exemplary embodiment, a "population to be sorted" is a heterogeneous population from which it is desired that one object type or category comprising the heterogeneous population be selected out so as to create at least one other, second, population that is homogeneous. In one exemplary embodiment, the population to be sorted comprises a heterogeneous population of objects some of which have a void in the interior. Thus, in an exemplary embodiment, objects without a void in the center are selected out of the population, thereby providing a homogeneous population comprising objects having a void in the center. Thus, in one exemplary embodiment, cherries comprising pits are selected out of a population of cherries, wherein the population of cherries comprises cherries without pits as well as cherries with pits. Thus in this embodiment, the population is sorted into a first class e.g., a population of cherries with pits (object without a void in the center), and a second class e.g., a population of cherries without pits (objects having a void in the center). Thus, a heterogeneous population to be sorted is sorted such that one object type or category comprising the heterogeneous population is selected out so as to create at least one other, second, population or class that is homogeneous.

The term "homogeneous population" or the term "homogeneous" as used herein typically refers to a population wherein at least about 80% of the objects comprising the population are of the same type or same category or same classification. In some exemplary embodiments a population is "homogeneous" when at least about 85% of the objects comprising the population are of the same type or same category or same classification. In other exemplary embodiments, a population is "homogeneous" when at least about 86%, 87%, 88%, or 89% of the objects comprising the population are of the same type or same category or same classification. In still other exemplary embodiments, a population is "homogeneous" when at least about 90%, 91%, 92%, 93%, 94%, 95%, 96%, 97%, 98%, 99%, or 100% of the objects comprising the population are of the same type or same category or same classification.

The term "agriculture" as used herein, refers broadly to human cultivation of plants and animals. Thus, "agriculture" as used herein, encompasses all aspects of plant and animal cultivation including but not limited to the science, art and/or occupation of plant cultivation, crop production, and livestock production. The products of agriculture e.g., a tomato plant; a tomato; fruit, e.g., cherries, apricots, peaches, etc; vegetables; a tomato seed; packaged tomato products e.g., stewed canned tomatoes; a cow; a side of beef; canned stew with beef; etc, are broadly referred to herein as "agricultural produce".

The term "agricultural process stream" as used herein refers to a flow or succession of agricultural objects or equivalently, a flow or succession of agricultural produce. Typically, objects comprising an "agricultural process stream" move or proceed continuously past a fixed point such that they can be detected and separated into different categories. In one exemplary embodiment, an "agricultural process stream" comprises canned goods e.g., canned fruit, canned vegetables, etc. In another exemplary embodiment, an "agricultural process stream" is a population of stone fruit e.g., cherries, apricots, peaches, etc, that comprises stone fruit with pits, and stone fruit which has had its pits removed e.g., pitted cherries, apricots, peaches, etc.

The term "microprocessor", or "micro-processor" as used herein, refers broadly without limitation, to a computer system, a computer equivalent, or a processor which is designed to perform arithmetic and/or logic operations using logic circuitry that responds to and processes the basic instructions that drive a computer. Thus, the term "microprocessor" refers to any device comprising a programmable digital electronic component that incorporates the functions of a central processing unit (CPU) on a single semiconducting integrated circuit (IC). Typical computer systems may comprise one or more microprocessors. Therefore, the term "microprocessor" as used herein, typically refers to a device comprising at least one microprocessor.

Thus, the expression "a microprocessor for applying a detection algorithm" as used herein refers to any microprocessor based means for deriving a decision based on the data from the photodiode outputs.

The term "conveying means" or "product feeding means" as used herein, refers to a structure, e.g., a vibrating hopper, alone or in combination with a slide, a slide, a rotating drum, conveyor belt etc., for singly delivering individual objects comprising "a population of objects to be sorted" to a region of space which in some embodiments is referred to as a "sensing area". The product feeding means is generally defined by the configuration of the process stream, e.g., stone fruit, e.g., cherries, apricots, plums, etc exiting a pitting machine. At the "sensing area" beams from an x-ray source are attenuated by the object to be sorted. Typically, the "product feeding means" delivers the product or object singly or individually to the sensing area where the singulated object is detected and subject to action by a diversion means. Therefore, the "product feeding means "singulates" the population of objects to be sorted. Thus, in one exemplary embodiment, the product feeding means delivers objects comprising a population to be sorted to the "sensing area" in single file.

The "x-ray density" as used herein refers to the ability of a sample material to attenuate x-ray photons.

The term "photodiode" as used herein refers to a device that absorbs light and generates a voltage at the output that depends on the amount absorbed.

The term "phosphor" as used herein refers to a material that absorbs x-ray photons and generates light photons, wherein the intensity of the light photons emitted depends on the intensity of the x-ray photons absorbed.

The term "detector" as used herein refers to any device that absorbs x-rays and generates a voltage output that is proportional to the amount of x-rays absorbed. In an exemplary embodiment, a "detector" is made of semiconductor crystals that respond directly to x-rays. In another exemplary embodiment, a "detector" is a member selected from the group consisting of a photodiode with a phosphor coating, in which the phosphor absorbs x-ray photons and emits visible light photons to which the photodiodes respond.

The term "detector array" as used herein refers to multiple x-ray detectors mounted side by side to form a continuous line.

The term "diversion means" or "sorting means" as used herein refers to a structure or the resultant physical action caused by a structure, that provides means for removing select objects from a population. Diversion means can be any suitable means for achieving the desired result e.g., diverting one class of objects from a population of objects to be sorted. Exemplary diversion means include, but are not limited to e.g., a blast of compressed air from an air nozzle, a mechanical arm or lever, a water jet, an air powered actuator, a hydraulic powered actuator, and etc.

I. Introduction:

X-ray sorting equipment is typically used in modern processing plants to remove contaminants and/or defects from agricultural commodities. The equipment is sophisticated, and unfortunately, expensive. Thus, producers of agricultural commodities are faced with high production costs for their finished product, and these production costs are passed on to consumers.

Figure 2:
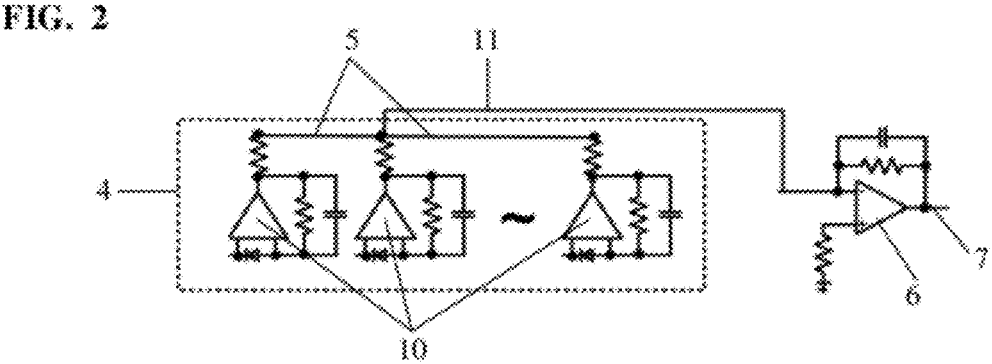
FIG. 2 An exemplary electronic circuit that records the sum of the outputs of an array of photodiode based x-ray detectors.

Fortunately, the present inventors have now discovered that by configuring the electronics to simply sum the outputs of the photodiodes, rather than tracking each individual output as is done in the case of the standard two-dimensional x-ray imaging systems discussed above, a much simpler one-dimensional signal is generated. In an exemplary embodiment, detectors (10) e.g., photodiodes, comprising a detector array (4) output voltage signals (5). The output signals (5) are summed by tying them together at a common point at the input (11) of a summing amplifier (6) as shown in FIG. 1 and FIG. 2. In an exemplary embodiment, the one-dimensional signal output from the summing amplifier (7) is observed on an oscilloscope. In another exemplary embodiment, the one-dimensional signal from the summing amplifier (7) is input to a microprocessor for processing and algorithm implementation. These approaches greatly reduce the size, complexity, and cost of the system by comparison to known systems that sort based on a two dimensional image.

Thus, an exemplary embodiment of the invention provides an apparatus for obtaining one-dimensional signals representing the average x-ray density across the width of any sample. In one exemplary embodiment, the apparatus is used to detect and divert cherries that have pits from a population comprising cherries with pits and cherries without pits.

Obtaining One-Dimensional X-Ray Density Signals:

In one aspect, the invention provides an apparatus for obtaining one-dimensional signals representing the average x-ray density across the width of any sample. In an exemplary embodiment that makes reference to FIG. 1 and FIG. 2, one-dimensional signals representing the average x-ray density across the width of any sample are generated by tying the outputs (5) from each detector (10) e.g., a photodiode, in a detector array (4) to the input (11) of a summing amplifier (6), thus providing a signal (7) that is the sum of the output voltages of all the detectors in the detector array (4). The output signal from the summing amplifier (7) is input to an oscilloscope or microprocessor (8) and periodically measured as the sample passes between the x-ray source and the detector array, thus generating the one-dimensional signal.

Although devices which measure x-ray density using photodiode based detectors are known in the art, e.g., linescan arrays and x-ray CCD cameras as discussed above (see e.g., Haff, R. P. and Slaughter, D. C. (2004) supra), the outputs of the photodiode detectors from known instruments are typically individually tracked to form a two-dimensional image.

In contrast, an embodiment of the invention records the sum of the detector outputs, thereby providing a one-dimensional (1D) signal instead of a two-dimensional (2D) image.

An exemplary linescan x-ray configuration is shown schematically in FIG. 1. Product (3) is conveyed between the x-ray source (1) and the linear detector array (4). Generated x-rays (2) are attenuated by the sample and incident on the detectors (10) e.g., photodiodes, which comprise the detector array (4). The output voltages (5) are tied to a common point and input (11) to a summing amplifier (6). The output signal (7) from the summing amplifier (6) is input to the microprocessor (8), which measures the output signal (7) at a rate that is synchronized to the speed of the product (3), and thus generating a one-dimensional signal. In an exemplary embodiment, the microprocessor (8) applies a detection algorithm that is unique to the nature of the product (3) and the defect or contaminant of interest. If appropriate, the microprocessor (8) generates a signal activating the diversion means (9). The direction of motion of the product (3) in FIG. 1 is either into or out of the plane of the paper.

FIG. 2 schematically shows the configuration for the detector array employed in the generation of a one dimensional X-ray signal as disclosed herein. The outputs of the detector (5) are tied to a common point and input (11) to a summing amplifier (6). The output (7) of the summing amplifier (6) is subsequently input into a microprocessor (8) as disclosed above in FIG. 1.

Figure 4:
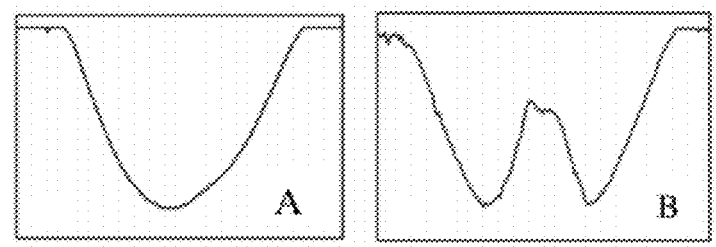
FIG. 4. Exemplary one-dimensional signals for cherries with and without pits.

Detection Algorithm:

Exemplary of the types of features that are detected by the apparatus disclosed herein include, those that generate signals similar to those in FIG. 4, e.g., objects with a void in the interior e.g., pitted stone fruits, marbles with holes in the center, etc. An algorithm has been developed and is disclosed herein, which simply counts the number of points at which the direction (derivative changes signs) of the signal changes, essentially counting the numbers of minima and maxima. For the case of a sample with no void, a single minima is expected, whereas for a sample with a void two minima and one maxima are expected (see e.g., FIG. 4B). The signal is transformed by binning, where the value in each bin is the average value of all data points within the range of the bin. This "binning" is done to eliminate artificial minima and maxima that are a consequence of noise. Starting at one end of the transformed signal, each point is compared to both the previous point and the next point. If the current point is either greater than both or less than both then it is counted as a turning point. If the sum of turning points is greater than one, the sample is classified as having a void. Varying the number of segments into which the original signal is divided in the smoothing process allows flexibility in the results in terms minimizing false positives (good classified as bad), false negatives (bad classified as good) or the total overall error.

Figure 3:
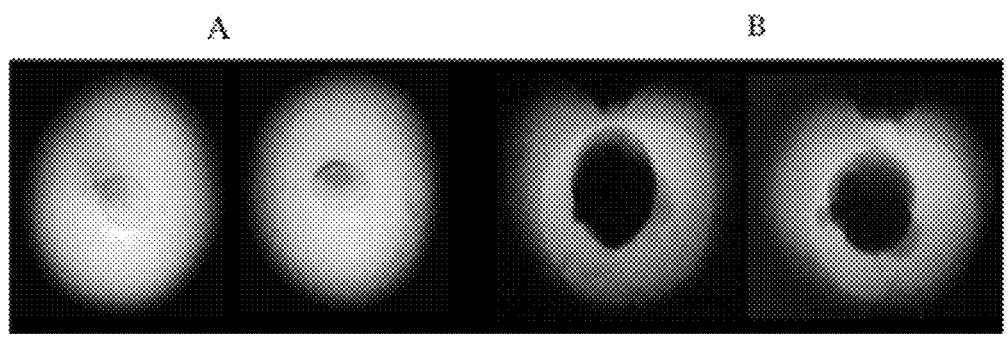
FIG. 3. Exemplary x-ray images showing the difference between cherries with pits and those without.

I. Apparatus for Detection of Pits in Cherries:

FIG. 3 shows conventional x-ray images of cherries with pits intact A and cherries that have been pitted B. The round dark region in the images of pitted cherries B represents the void left behind after the pit is removed. FIG. 4 shows the corresponding signals generated when the one-dimensional detector configuration disclosed herein is employed, for both a cherry with the pit intact A and after pitting B. This exemplifies an example of a sorting task in which the spatial resolution of the two-dimensional image is not required to accomplish the required task.

EXAMPLES

Example 1

The following simple example illustrates the accuracy of detecting remaining ("missed") pits in pitted cherries using the detector configuration disclosed herein. The signals expected from the detector configuration disclosed herein can be simulated from x-ray images by summing pixel values within each column. Fresh cherries were pitted with a 1manual cherry stoner and x-rayed on film at 28 keV for three minutes. The film images were digitized using a film scanner. A one dimensional signal was generated for each image by summing the pixel values within each column. Signals were generated for 150 pitted and 150 unpitted cherries. These signals were arranged as plots in random order and inspected by six human subjects who tried to score them as either pitted or unpitted. Human recognition is used in this exercise to demonstrate the feasibility of pit detection using one-dimensional signals. The developed algorithm was also tested on this dataset and results compared to those achieved by visual inspection of the signals.

The results for six subjects for inspection of one dimensional x-ray signals are shown in Table 1. The results indicate near perfect detection of pits with an average false positive rate of around 3%. The best subject correctly detected all pits with a false positive rate of 1.5%. Results using images were perfect for all six subjects, indicating some loss of information in the transformation. These results strongly indicate that a significant difference exists between the two classes of signals, and that algorithm development is practical.

TABLE 1

Results of human inspection of generated signals.

| Subject | % False Positive | % False Negative | Total Error |
|---|---|---|---|
| 1 | 3.6 | 0 | 3.6 |
| 2 | 2.1 | 0 | 2.1 |
| 3 | 1.5 | 0 | 1.5 |
| 4 | 1.5 | 1.5 | 3.0 |
| 5 | 6.7 | 0 | 6.7 |
| 6 | 3.6 | 1.5 | 5.1 |
| Average | 3.2 | 0.5 | 3.7 |

The results of applying the algorithm to the same data are shown in Table 2. The algorithm was applied with various values of the number of points in the smoothed signal (column 1) and the results sorted by either false positive, false negative, or overall error. In terms of lowest false positive and lowest overall error the algorithm achieved better results than human observers, albeit at the cost of somewhat higher false negatives.

TABLE 2

Results of algorithm application on generated signals. Best 10 results shown.

| Sorted by FP | | | | Sorted by FN | | | | Sorted by Tot. Error | | | |
|---|---|---|---|---|---|---|---|---|---|---|---|
| #PTS | FP % | FN % | Tot % | #PTS | FP % | FN % | Tot % | #PTS | FP % | FN % | Tot % |
| 10 | 0 | 11.3 | 8.5 | 23 | 6 | 2.7 | 3 | 23 | 6 | 2.7 | 3.5 |
| 7 | 0 | 20 | 15 | 24 | 6 | 2.7 | 3 | 24 | 6 | 2.7 | 3.5 |
| 8 | 0 | 20.7 | 15.5 | 25 | 6 | 2.7 | 3 | 25 | 6 | 2.7 | 3.5 |
| 5 | 0 | 71.3 | 53.5 | 21 | 8 | 2.7 | 4 | 17 | 4 | 4 | 4 |
| 6 | 0 | 72 | 54 | 22 | 8 | 2.7 | 4 | 18 | 4 | 4 | 4 |
| 12 | 2 | 6 | 5 | 26 | 8 | 2.7 | 4 | 19 | 6 | 3.3 | 4 |
| 17 | 4 | 4 | 4 | 27 | 8 | 2.7 | 4 | 20 | 6 | 3.3 | 4 |
| 18 | 4 | 4 | 4 | 28 | 8 | 2.7 | 4 | 29 | 6 | 3.3 | 4 |

What is claimed is:

1. An apparatus for sorting objects comprising a heterogeneous population to be sorted wherein one object type or category comprising the heterogeneous population is selected out so as to create at least one other, second, population or class that is homogeneous, the apparatus comprising:
   (i) an x-ray source capable of generating an x-ray,
   (ii) a conveying means for conveying the objects comprising a population to be sorted to a sensing area,
   (v) a linear array of x-ray detectors configured so that the voltage outputs of each detector are tied to the same point, and input to a summing amplifier, which generates a summing amplifier signal,
   (iv) a microprocessor for applying a detection algorithm, wherein
      the summing amplifier output signal is input to the microprocessor, thereby generating a one dimensional image of an object to be sorted,
   (v) a means for viewing the one dimensional image of an object to be sorted, and
   (vi) a sorting means or a diversion means,
   wherein the x-ray source is configured to generate an x-ray, and
   wherein the x-ray is configured to target the sensing area such that an object in the sensing area is positioned such that the x-ray is incident thereon, and
   wherein the linear array of x-ray detectors is located with respect to the x-ray source and the sensing area such that the linear array of x-ray detectors is capable of detecting an x-ray generated by the x-ray source that is targeted at the sensing area.

2. The apparatus of claim 1, wherein the population to be sorted comprises an agricultural process stream.

3. The apparatus of claim 1, wherein agricultural process stream comprises objects that are members of the group consisting of pitted and unpitted fruits, and canned goods.

4. The apparatus of claim 1, wherein the population comprises any object that may contain unwanted internal voids of sufficient size to significantly reduce the mean x-ray density in that region of the sample.

5. The apparatus of claim 1, wherein the product feeding means is a member selected from the group consisting of a slide, a conveyor belt, and a rotating drum.

6. The apparatus of claim 1, wherein an x-ray detector is a member selected from a group consisting of phosphor coated photodiodes and direct detection semiconductors.

7. A method for detecting inclusions in agricultural produce the method comprising:
   (1) loading the agricultural produce onto an apparatus for sorting objects,
      wherein the apparatus comprises:
      (i) an object feeding means,
      (ii) an x-ray source capable of generating an x-ray,
      (iii) a conveying means for conveying the object comprising a population to be sorted to a sensing area,
      (iv) a linear array of x-ray detectors configured so that the voltage outputs of each detector are tied to the same point, and input to a summing amplifier, which generates a summing amplifier output signal,
      (iv) a microprocessor for applying a detection algorithm,
      wherein
         the summing amplifier output signal is input to the microprocessor, thereby generating a one dimensional image of an object to be sorted,
      (v) a microprocessor for applying a detection algorithm, (vi) a means for viewing the one dimensional image of an object to be sorted, and
(vi) a diversion means,
wherein the x-ray source generates an x-ray, and
wherein the x-ray is targeted at the sensing area such that an object in the sensing area has the x-ray incident thereon, and
wherein the linear array of x-ray detectors is located with respect to the x-ray source and the sensing area such that the linear array of x-ray detectors is capable of detecting an x-ray generated by the x-ray source that is targeted at the sensing area, and
(2) activating the apparatus such that the product feeding means delivers the agricultural produce to the conveying means in single file, the conveying means conveys the agricultural produce to the sensing area,
wherein,
the agricultural produce is targeted with an x-ray in the sensing area and the x-ray is incident on the agricultural produce,
the x-ray passes through the agricultural produce and is incident on the linear array of x-ray detectors,
thereby generating a one dimensional image of the agricultural produce that is subjected to processing by the detection algorithm and displayed on the means for viewing the one dimensional image of an object such that an inclusion, if present, is detected.

8. The method of claim 7, further comprising:
(3) diverting agricultural produce comprising inclusions by activating the diversion means.

\* \* \* \* \*